United States Patent [19]

Baierl

[11] 4,159,223
[45] Jun. 26, 1979

[54] USE OF ACTIVATED CARBON TO RECOVER AND SEPARATE CHEMICALS PRODUCED DURING PULPING OPERATIONS

[75] Inventor: Kenneth W. Baierl, Marysville, Wash.

[73] Assignee: Scott Paper Company, Philadelphia, Pa.

[21] Appl. No.: 622,796

[22] Filed: Oct. 16, 1975

Related U.S. Application Data

[63] Continuation of Ser. No. 178,889, Sep. 9, 1971, abandoned.

[51] Int. Cl.$^2$ ............................................. D21C 11/02
[52] U.S. Cl. .......................................... 162/14; 162/16; 162/29; 210/40
[58] Field of Search ........................ 162/14, 15, 16, 29; 210/31 R, 39, 40

[56] References Cited

U.S. PATENT DOCUMENTS

| | | | |
|---|---|---|---|
| 2,585,491 | 2/1952 | Olsen | 210/31 R |
| 2,585,492 | 2/1952 | Olsen | 210/31 R |
| 2,710,254 | 6/1955 | Van Blaricom et al. | 162/16 |
| 3,223,748 | 12/1965 | Bohrer | 210/31 R |
| 3,436,344 | 4/1969 | Canning et al. | 210/39 |

OTHER PUBLICATIONS

Timpe, W. G. et al., "The Use of Activated Carbon for Water Renovation in Kraft Pulp and Paper Mills," Presented at Seventh TAPPI Air & Water Coference, 6/1970.

Primary Examiner—S. Leon Bashore
Assistant Examiner—William F. Smith
Attorney, Agent, or Firm—Nicholas J. DeBenedictis; John W. Kane, Jr.

[57] ABSTRACT

Chemicals produced during pulping operations are recovered and separated by passing chemical-containing liquors from said operations through one or more units containing activated carbon. The chemicals are recovered from said units by introducing a solvent into said unit and separating the materials removed therefrom in a fractionating column.

13 Claims, 2 Drawing Figures

USE OF ACTIVATED CARBON TO RECOVER AND SEPARATE CHEMICALS PRODUCED DURING PULPING OPERATIONS

This is a continuation of application Ser. No. 178,889, filed Sept. 9, 1971, now abandoned.

BACKGROUND OF THE INVENTION

1. Field of the Invention

The present invention relates generally to a method of treating chemical-containing liquors from pulping operations to remove the chemicals contained therein, and to a method of recovering said chemicals. More particularly the invention relates to passing liquors, containing chemicals produced during pulping operations, through one or more units containing activated carbon to remove and separate the chemicals present in said liquors. The chemicals are subsequently recovered from the activated carbon units by introducing a solvent into the unit.

2. Description of the Prior Art

In the preparation of wood pulp useful in paper-making operations wood chips are treated, either chemically or mechanically, to separate the cellulosic fibers. In the sulfate, or kraft, pulping process wood chips are treated with a cooking liquor containing sodium hydroxide, sodium sulfide and sodium carbonate. In the sulfite pulping process wood chips are treated with a cooking liquor containing sulfur dioxide, sulfurous acid and bisulfite, usually as sodium, calcium, magnesium or ammonium bisulfite. The chemicals attack the non-fibrous materials present in the wood chips, reacting with the lignin to form water-soluble compounds, thereby allowing separation of the fibrous, or cellulosic, portion of the chips.

The treatment of the wood chips normally takes place in a digester over an extended period of time and at an elevated temperature. The exact time, temperature and pressure depend, to a considerable extent, on the species of wood and the amount of chemicals employed. To maintain a constant temperature and pressure during the chemical treatment, vapors are periodically released from the digester. Also, before the pulp is discharged from the digester the temperature and pressure are lowered by releasing additional vapors. All of these vapors are collected in high pressure accumulators and are commonly referred to as digester relief gases. The pulp and spent pulping liquor can be removed from the digester by being blown out at low pressure or dumped. During their removal additional vapors are released which are commonly referred to as digester blow gases. The digester blow gases can be condensed and the condensate collected in a hot water accumulator where it is allowed to cool and overflow into a drain. This overflow is commonly referred to as hot water accumulator overflow. The digester relief gases, digester blow gases, spent pulping liquor and hot water accumulator overflow contain chemical by-products of the pulping operation including, for example, sulfur dioxide, methanol, acetone, acetaldehyde, ethanol, furfural, p-cymene, acetic acid, dimethyl disulfide, dimethyl sulfide, methyl mercaptan, crude turpentine and hydrogen sulfide. The type and amount of chemical in any given sample depends on many factors including the species of wood, treatment chemicals and cooking conditions employed. After the fibrous pulp is separated, the cooking liquor, now commonly referred to either as spent kraft pulping liquor (or black liquor) or spent sulfite pulping liquor, depending on the pulping process employed, must be disposed of. In disposing of these liquors as well as the condensed gases described above, both economic and environmental factors must be considered. Much effort has been expended in recent years to find an economical and practical means for disposing of, for example, the spent kraft pulping liquor. The most commonly employed treatment is the evaporation of the liquors to recover the sodium salts present therein for reuse in subsequent pulping operations. The evaporator condensates and vent gases from this treatment are also known to contain various chemicals produced during the pulping operation.

The recovery of saleable by-products from the liquors and condensates produced during kraft pulping operations has been suggested. The recovery of crude turpentine, or pinene, from the relief gases of kraft digesters is well known. See for example, Casey, *Pulp and Paper*, Vol. 1, second edition, Interscience Publishers, Inc., New York, (1960) pages 284–285. However, no commercially acceptable process for recovering all of these chemicals has heretofore been available. Most of the prior art processes recovered only one of the chemicals and the purity of the recovered chemicals was poor requiring further processing to obtain saleable products.

Much effort has also been expended to find an economical and practical means of disposing of spent sulfite pulping liquor. Use of the spent sulfite pulping liquor as a road binder has been suggested as a solution to the problem. The recovery of saleable by-products has also been suggested. However, the most commonly used treatment is evaporation and subsequent burning of the concentrated liquor to produce steam and power for use in subsequent pulping operations and to recover chemicals, such as sulfur dioxide and sulfites, also for use in subsequent pulping operations.

Spent sulfite pulping liquors are known to contain, besides sulfur dioxide, organic chemicals such as methanol, ethanol, acetic acid, furfural and p-cymene. These organic compounds are formed as by-products of the pulping process. It has previously been suggested that these chemicals be recovered from the spent sulfite pulping liquor. However, no commercially acceptable process for recovering these chemicals has heretofore been available. Most of the prior art processes recovered only one of these chemicals and to recover all of them would require a series of treatments. Also, the purity of the organic chemicals recovered by the previously known processes has been poor and further processing was often required to obtain saleable products.

In U.S. Pat. No. 1,838,109, issued to Richter, furfural was obtained as a by-product in the preparation of wood pulp by the sulfite pulping process. The furfural was recovered by heating the spent pulping liquor, at an acid pH, to a temperature sufficient to vaporize the furfural and then condensing the vaporized furfural. This process required temperatures in excess of 250° F., which often resulted in decomposition of the furfural. Also, the acid pH required was achieved by the use of sulfur dioxide gas, the presence of which has now been found to have a deleterious effect on the furfural produced. Other chemicals in the spent sulfite pulping liquor were not recoverable by this process.

In U.S. Pat. No. 1,223,158, issued to Enger, the "hydrocarbon cymol" was isolated from digester relief gases obtained from a sulfite pulping process by allowing the condensed gases to stand in a plurality of tanks during which time the cymol came to the top and could be separated. The liquor was then returned to the digester. The purpose of this process was not to recover the organic chemical but rather to purify the condensate so it could be reused in subsequent pulping operations.

In U.S. Pat. No. 1,833,955 issued to Richter, alcohol (ethanol) was obtained by fermentation of the sugars contained in partially evaporated spent sulfite pulping liquor.

However, there has not heretofore been available a method for recovering and separating chemicals produced during both sulfite and kraft pulping operations.

Activated carbon has been used for water purification, including the treatment of pulp and paper mill effluents. When working with these effluents the purpose of the activated carbon treatment has included the removal of color and odor and the reduction of the chemical oxygen demand and the biological oxygen demand of the effluents. However, it has not heretofore been suggested to utilize activated carbon treatments to remove and separate, in a useable form, the chemicals present in pulp mill effluents.

A commercially acceptable activated carbon separation process has not been available due, at least in part, to the absence of a satisfactory method for regenerating the activated carbon. Previously available regeneration techniques included the use of regeneration furnaces, wet air oxidation and caustic soda washing. These techniques are time consuming and expensive, and result in at least partial destruction of the chemicals removed from the carbon.

SUMMARY OF THE INVENTION

In accordance with the present invention chemicals produced during pulping operations are recovered and separated by passing chemical-containing liquors from said operations through one or more units containing activated carbon. It should be understood that the term "liquors" as used herein includes both liquors and condensed gases produced during pulping operations. The chemicals are recovered from said units by introducing a solvent into said unit, and separating the materials removed therefrom in a fractionating column. The quality of the recovered chemicals and the chemical loading of the units containing activated carbon are improved by a preliminary treatment of the chemical-containing liquors with steam prior to the introduction of said liquors into the activated carbon units. When utilizing liquors from sulfite pulping operations, a further improvement is noted when the liquors are treated with a strong base prior to the introduction of said liquors into the activated carbon units. When utilizing liquors from kraft pulping operations, a further improvement is noted when the liquors are treated with a strong acid prior to the introduction of said liquors into the activated carbon units.

DESCRIPTION OF THE PREFERRED EMBODIMENTS

According to the present invention, the liquors and condensed gases produced during pulping operations are subjected to a treatment which recovers and separates the chemicals contained therein. The chemicals which can be separated by this process depend to a considerable extent on factors such as the wood species, chemicals and cooking conditions employed in the pulping operations. Liquors which can be employed include spent kraft pulping liquor, spent sulfite pulping liquor, condensed digester relief gases, condensed digester blow gases, condensate from spent liquor evaporators and hot water accumulator overflow.

The chemicals recovered include, for example, furfural, acetic acid, methanol, saccharic acid, lactones, tall oil and crude turpentine comprising primarily $\alpha$-terpineol and $\alpha$-pinene. In general, any liquor containing the above-mentioned chemicals or combinations thereof can be treated in accordance with the present invention.

Figure 1:
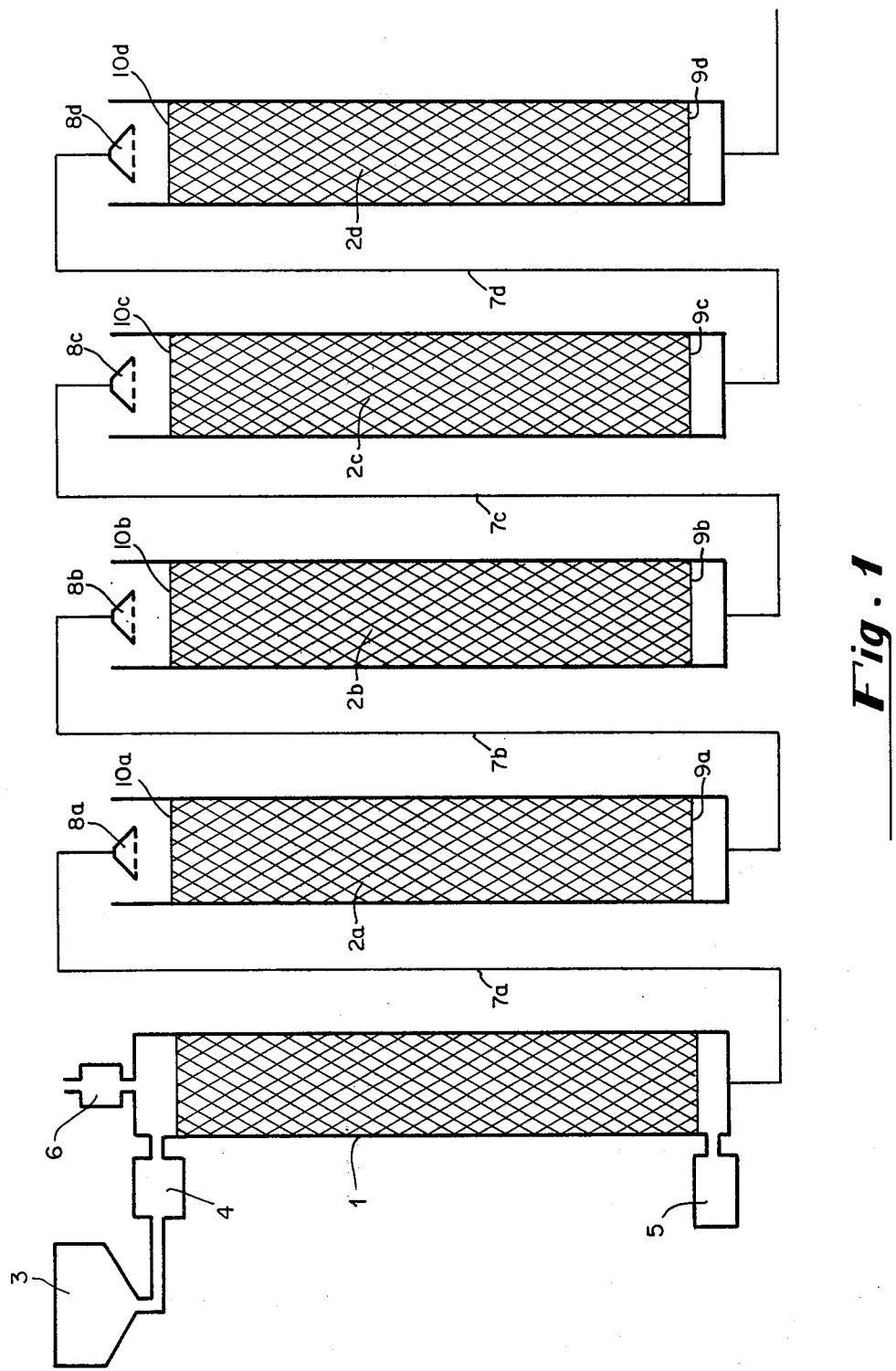
FIG. 1 is a schematic representation of a series of activated carbon-containing units useful for recovering and separating chemicals in accordance with the present invention.

Chemicals produced during pulping operations and contained in the above-mentioned liquors are recovered and separated by first passing the liquors through one or more units containing activated carbon. The units which may be employed include columns packed with granular activated carbon, expanded beds of activated carbon and slurry systems containing powdered activated carbon. It is especially preferred as shown in FIG. 1 to employ a series of tubular columns the diameter and height of which are varied in accordance with the volume of liquor being treated. The number of units employed depends on several factors such as the type and amount of chemicals present in the liquors, the rate at which the liquors are introduced into the units, the temperature of the liquors and the chemicals to be recovered. The columns are packed with fresh, wet, deaerated, activated carbon. In operation, chemical-containing liquors are introduced into the first unit at a rate dependent on the size of said unit. When working with columns having an inside diameter of 4 inches and a height of 48 inches and packed with 7.1 pounds of activated carbon, the liquors are introduced at a rate of about 0.21 gallons per minute. The liquors pass down the column, are removed from the lower end thereof and are pumped to the next unit in the series. When working with liquors from sulfite pulping operations, it is especially preferred to utilize from two to four units in the series since the liquors from these operations generally contain relatively substantial amounts of furfural, actic acid and methanol. It has been found that when the liquors are introduced into the units in a liquid form the first unit retains furfural, the second unit retains acetic acid and the third and fourth units, when used together retain methanol, with reuseable water being discharged from the fourth unit. It has also been found that when the liquors are introduced into the unit or units as a vapor, the first column retains acetic acid and methanol and furfural pass through the units. Thus by introducing the liquors as either a liquid or a vapor the chemical separation and recovery can be varied.

The chemicals are recovered from the units containing activated carbon by a process which comprises introducing a solvent into one of the units and separating the materials removed from said unit in a fractionating column. It is especially preferred to partially vaporize the solvent before it is introduced into the unit. In practice, recovery of the adsorbed chemicals is achieved by removing one of the units containing activated carbon from the series, allowing any excess liquor contained in said unit to drain out, and then introducing a vaporized solvent into said unit. Suitable solvents include ethanol, methanol, acetone, benzene and ethers. The particular solvent chosen is one which is best able to remove the particular chemical from the unit in question, or to react with the chemical to form a product which, in turn, is removable from the unit. After the particular chemical and solvent are removed from the unit, they are introduced into a fractionating column where they are separated.

The frationating column is preferably a tubular column the diameter and height of which are varied in accordance with the volume of liquor being treated. The column is packed with a conventional packing such as bubble caps; sieve trays; Goodloe 316SS, a wire mesh packing available from Packed Column Corporation, Springfield, N.J.; or ¼ inch ceramic saddles available from U.S. Stoneware, Inc., Akron, Ohio. In an especially preferred apparatus, means for introducing steam into the fractionating column are attached to the lower end of the column, and a condenser is located on the top of said column to prevent loss of the volatile organic compounds. Means on the side of the column, preferably at a point above the middle of said column, are designed for introducing material into the column. It has been found that the separation of the compounds present in said material is improved if the material is preheated prior to its introduction into the fractionating column. For this reason it is especially preferred to include a preheater for the liquors being introduced into the column. Two taps and internal means for the removal of the volatile organic compounds separated from the liquors are located, one above the other, on the side of the column above the point where the liquors are introduced into said column. The upper tap is designed for the removal of more volatile organic compounds, such as methanol, and the lower tap for the removal of less volatile organic compounds, such as furfural.

Prior to their introduction into the unit, or units, containing activated carbon it is preferred to treat the liquors with steam in a steam stripper. This treatment removes at least part of those materials, such as hydrogen sulfide and sulfur dioxide, which would otherwise interfere with the purity of the recovered chemicals.

An apparatus which is especially preferred for carrying out this treatment is a steam stripper which comprises a tubular column, the diameter and height of which are varied in accordance with the volume of liquor being treated. The column is packed with a conventional packing such as bubble caps; sieve trays, Goodloe 316SS, a wire mesh packing available from Packed Column Corporation, Springfield, N.J.; or Intalox ¼ inch ceramic saddles available from U.S. Stoneware, Inc., Akron, Ohio. In this especially preferred apparatus, means for introducing steam are attached to the lower end of said column and a means for collecting gases removed from the liquor are attached to the upper end of the column. Means, preferably near the upper end of the column, are designed for introducing liquors into the column. It has been found that the separation is improved if the liquors are preheated prior to introduction into the steam stripping column. For this reason it is especially preferred to include a preheater for the liquors being introduced into the column.

In operation liquors are introduced into the steam stripping column at a rate dependent on the size of said column. When working with a column having an inside diameter of 4 inches and a height of 4 feet, the liquors are introduced at a rate of from about 1.0 gallons per minute to about 2.0 gallons per minute. Steam is simultaneously introduced into the column in an amount equal to from about 1.0% to about 5.0% of the weight of the liquor. As the liquor passes down the column the steam removes gases, such as sulfur dioxide and hydrogen sulfide, contained in said liquor. The stripped liquor passes from the lower end of the column to the fractionating column described above. The gases pass out the top of the column and are collected. Referring now to the drawings, FIG. 1 is a schematic representation of a series of activated carbon-containing units useful for recovering and separating chemicals in accordance with the present invention. The apparatus comprises a steam stripper 1 and four activated carbon-containing columns 2a, 2b, 2c, and 2d. In operation chemical-containing liquors from pulping operations are collected in a storage unit 3 from which they are fed, through a feed preheater 4, into the top of the steam stripper. A steam source is attached to the lower end of the steam stripper and an outlet 6 for the removal of gaseous materials is attached to the upper end of the stripper. After treatment with steam in the steam stripper the liquors pass through a line 7a and a spray nozzle 8a into the first activated carbon-containing column 2a. The column is packed with activated carbon above a support screen 9a. A distribution screen 10a for the liquor entering the column is located at the top of the activated carbon. After passage through the first column the liquor passes through a line 7b and a spray nozzle 8b into the second activated carbon-containing column 2b which also is packed with carbon between a support screen 9b and a distribution screen 10b. From the second column the liquor passes through a line 7c and a spray nozzle 8c into the third activated carbon-containing column 2c which is packed with carbon between a support screen 9c and a distribution screen 10c. The liquor from the third column passes through a line 7d and a spray nozzle 8d into the fourth activated carbon-containing column 2d which is also packed with carbon between a support screen 9d and a distribution screen 10d. Water leaving the fourth column is recycled for use in subsequent operations or disposed of essentially free of the chemicals previously contained therein.

Figure 2:
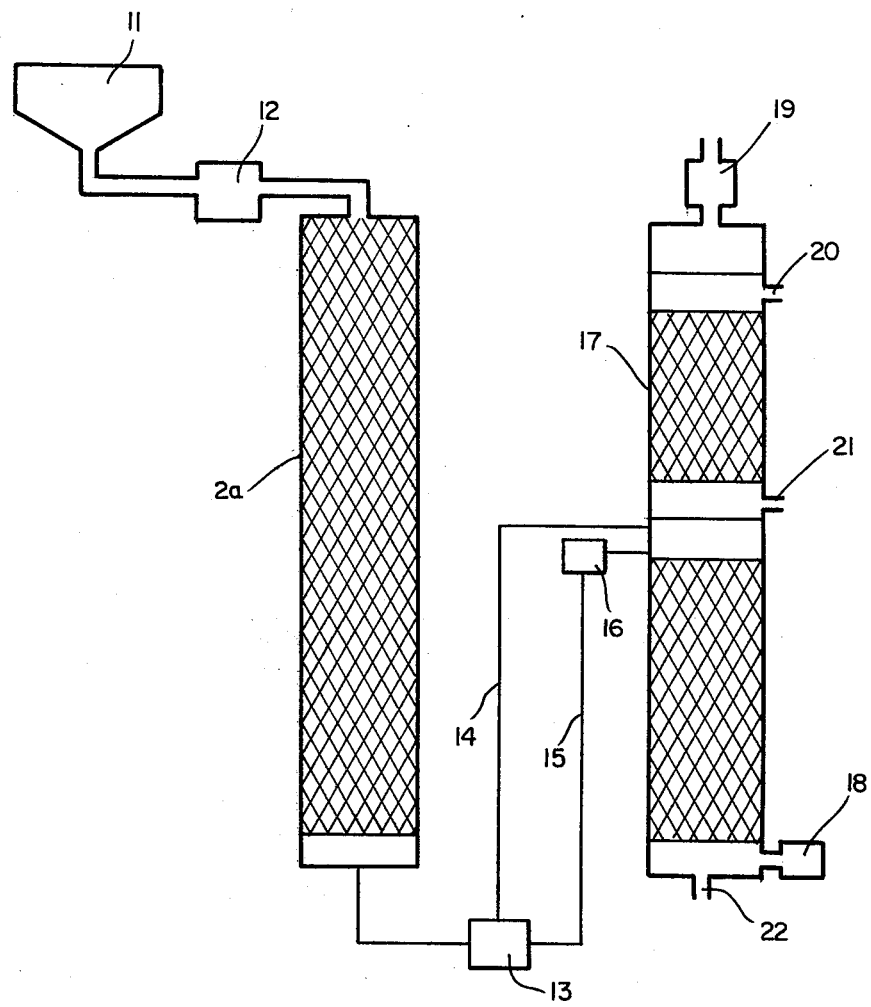
FIG. 2 is a schematic representation of an installation of apparatus arranged to recover chemicals from the activated carbon-containing units in accordance with the present invention.

FIG. 2 is a schematic representation of an installation of apparatus arranged to recover chemicals from the activated carbon-containing units. The apparatus comprises a solvent storage unit 11 from which solvent is fed through a heater 12 in which the solvent is at least partially vaporized into a chemical-containing, activated carbon unit 2a. The solvent/chemical mixture leaving the bottom of the unit enters a receiver 13 from which the vapors are fed directly through a line 14 into a fractionating column 17. The liquid portion of the mixture in the receiver is also fed through a line 15 and a feed preheater 16 into the fractionating column 17. The fractionating column has a steam source 18 attached to the lower end of the column and a condenser 19 attached to the top. Two taps 20 and 21 for the removal of the volatile organic compounds are located on the side of the column. The upper tap 20 is designed for the removal of the more volatile organic compounds and the lower tap 21 for the removal of the less volatile organic compounds. An outlet 22 is provided at the bottom of the column for the removal of any residual material such as water from the column.

In order to describe the present invention so that it may be more clearly understood, the following examples are set forth.

EXAMPLE I

A mixture of wood chips consisting of 66% softwood (spruce and balsam fir) and 34% hardwood (birch) were reduced to a pulp by the sulfite pulping process. The spent sulfite pulping liquor was collected and evaporated to a solids content of from 10% to 50%. The evaporator condensate was collected and introduced into the top of a steam stripper. The stripper consisted of a tubular glass column having an inside diameter of 4 inches and a height of 82 inches and was packed with 30 inches of Goodloe 316SS packing and 18 inches of Intalox ¼ inch ceramic saddles. Steam was simultaneously introduced into the lower end of the steam stripper. As the evaporator condensate passed down the column the steam removed the sulfur dioxide present in the condensate. The steam stripped evaporator condensate removed from the bottom of the stripper contained the following chemicals in which the percentages are percent by weight:
methanol—0.05%
acetic acid—0.53%
furfural—0.05%
water—99.37%

The steam stripped evaporator condensate was passed through a series of four glass columns containing activated carbon. Each column had an inside diameter of 4 inches and a height of 48 inches and was packed with about 7.1 pounds of fresh, activated carbon which had been deaerated by cooking in water at a temperature of from about 185° F. to about 210° F. overnight (approximately 15 hours). The carbon was supported on 20 mesh screens positioned 3 inches above the bottom of the column. The total height of carbon in each column was about 39 inches, and a distribution screen was located on the top of the carbon in each column.

The steam stripped evaporator condensate was introduced into the top of the first column at a rate of 0.21 gallons per minute through a spray nozzle. During continuous operation the liquid level in each column was adjusted to about 3 inches above the distribution screen. After 15 minutes methanol appeared in the effluent from the first column whereas acetic acid, furfural and the material responsible for the orange brown color of the liquor were retained by the carbon in the column. After one hour the effluent from the first column contained both methanol and acetic acid and the effluent from the second, third and fourth columns contained only methanol and water. No furfural was found in the effluent from the first column, even after 5 to 10 hours of operation. The results are shown in the following table:

TABLE I

| Column Number | Hours of Continuous Operation | Feed (% by weight) | | | | Discharge (% by weight) | | | |
|---|---|---|---|---|---|---|---|---|---|
| | | Furfural | Acetic Acid | Methanol | Water | Furfural | Acetic Acid | Methanol | Water |
| 1 | 5 | .05 | .53 | .05 | 99.37 | — | .53 | .05 | 99.42 |
| 2 | 1 | — | .05 | .05 | 99.90 | — | — | .05 | 99.95 |
| 3 | 1 | — | — | .05 | 99.95 | — | — | .03 | 99.97 |
| 4 | 1 | — | — | .03 | 99.97 | — | — | trace | 99.99 |

EXAMPLE II

An activated carbon column, similar to the first column described in Example I, which had absorbed 4.55 pounds of furfural from chemical-containing liquors resulting from a sulfite pulping operation was regenerated using methanol in accordance with the following procedure. Residual liquor was first allowed to drain from the column and methanol was introduced into the column to displace any additional liquor contained therein. A second portion of methanol was pumped from a storage tank through a heat exchanger where it was heated to a temperature of 200° F. and introduced as a vapor into the top of the furfural-containing carbon column. A mixture of liquid and vapor comprising furfural and methanol was removed from the bottom of the column and collected in a receiver. The vapor from the receiver was fed directly into a fractionating column and the liquid, after being preheated, was also introduced into the fractionating column. The fractionating column consisted of a tubular glass column having an inside diameter of four inches and a height of 260 inches. The column was packed with 144 inches of ¼ inch Untalox ceramic saddles available from V.S. Stoneware Inc., Akron, Ohio at the lower end, i.e., below the point at which material was introduced into the column, and 48 inches of Goodloe 316SS a wire mesh packing available from Packed Column Corporation, Springfield, N.J. A steam reboiler was located at the bottom of the column. Methanol was refluxed in the fractionating column causing it to separate from the furfural. Methanol was removed from a tap located near the top of the fractionating column and was returned to the storage unit for use in subsequent operations. Furfural was also removed from the column by a tap located above the point at which the materials were introduced into said column.

The amount of furfural, which was 90.3% by weight pure furfural, recovered from the fractionating column was equal to 4.27 pounds. Another 0.15 pounds of furfural was recovered from the fractionator as furfural saturated liquid. The total furfural recovered was equal to 97.3% of the furfural absorbed by the activated carbon.

Residual methanol was removed from the column containing activated carbon and the carbon was reactivated for use in subsequent operations by passing steam through said column.

EXAMPLE III

A column containing activated carbon, similar to those described in Example I, which had absorbed 6.68 pounds of acetic acid from chemical-containing liquors resulting from a sulfite pulping operation was regenerated using ethanol denatured with methanol as the solvent.

Residual liquor was first allowed to drain from the column and ethanol was introduced into the column to displace any additional liquor contained therein. A second portion of ethanol was pumped from a storage tank, through a heat exchanger where it was heated to a temperature of 200° F. and introduced as a vapor into the bottom of the acetic acid-containing column. A mixture of chemicals comprising ethanol and ethyl acetate was removed from the column and introduced into a fractionating column similar to that described in Example II. Ethyl acetate was removed from the tap located near the top of the fractionating column and ethanol from the lower tap.

The amount of ethyl acetate, which was 44% by weight ethyl acetate and 56% methanol, was equal to 100% of the theoretical amount of ethyl acetate expected from the column.

Residual denatured ethanol was removed from the column containing activated carbon and the carbon was reactivated for use in subsequent operations by passing steam through said column.

EXAMPLE IV

A column containing activated carbon, similar to that described in Example III was treated as described in Example III utilizing a water/methanol solvent in place of the denatured alcohol. A mixture of chemicals comprising methanol, water, acetic acid and methyl acetate was removed from the column and introduced into a fractionating column. By maintaining a high ratio of water to methanol in the fractionating column and thereby taking advantage of the reversibility of the reaction between methanol and acetic acid it was possible to recover an aqueous acetic acid solution containing 22% by weight acetic acid from the fractionating column.

EXAMPLE V

A mixture of wood chips consisting of 80% hemlock and 20% white fir were reduced to a pulp by the sulfite pulping process. The hot water accumulator overflow was collected and treated in a steam stripper as described in Example I. The steam stripped hot water accumulator overflow was vaporized by heating to a temperature of from about 100° C. to about 110° C. The vaporized material was introduced, at a rate equal to approximately 1 liter per hour, into a column containing activated carbon. The column was similar to those described in Example I. After one hour methanol and furfural were found in the effluent from the column whereas acetic acid was retained on the carbon in the column. After approximately 16 hours of continuous operation acetic acid was detected in the effluent from the column.

EXAMPLE VI

Douglas fir wood chips are reduced to a pulp by the kraft pulping process. The kraft spent pulping liquor is collected and found to contain alkali lignin, sodium acetate, sodium formate, lactate, methanol lactones, saccharinic acid, turpentine, tall oil, and some unidentified polymerized material. The liquor is treated in the steam stripper described in Example I and the steam stripped liquor is passed through a series of four glass columns containing activated carbon as described in Example I. The activated carbon retains saccharinic acid, lactones, turpentine and tall oil. The chemicals retained by the carbon are recovered as in Example II by passing an at least partially vaporized solvent through the column and separating the materials recovered in a fractionating column.

What is claimed is:

1. A method for recovering and separating chemicals produced during sulfite pulping operations which comprises
   passing liquors from said operations containing at least three chemicals to be recovered and separated through at least three units containing activated-carbon,
   separating the first chemical in said liquors with the first activated-carbon containing unit,
   separating the second chemical in said liquors with the second activated-carbon containing unit,
   separating the at least one remaining chemical in said liquors with the at least one remaining activated-carbon containing unit, and
   separately recovering the first, second and at least one remaining chemical from their respective units containing activated-carbon by introducing a solvent into each unit and subsequently separating the chemicals from the solvent.

2. A method, as claimed in claim 1, in which the chemical containing liquors are treated with steam prior to introduction into the units containing activated carbon.

3. A method, as claimed in claim 1, in which four units containing activated carbon are arranged in series. edition, 4. A method, as claimed in claim 1, in which the liquors containing at least three chemicals are produced during sulfite pulping operations wherein said liquors contain furfural, acetic acid and methanol and wherein the furfural is separated in the first unit containing activated-carbon, acetic acid is separated in the second unit containing activated-carbon, methanol is separated in the at least one remaining unit containing activated-carbon and water is discharged from the last unit containing activated-carbon.

5. A method, as claimed in claim 4, in which the liquors are introduced into the unit as a vapor.

6. A method, as claimed in claim 1, in which the chemicals are recovered from the unit containing activated carbon by introducing a solvent selected from the group consisting of methanol, ethanol, acetone and benzene into said unit and subsequently separating the chemical from the solvent in a fractionating column.

7. A method, as claimed in claim 6, in which the solvent is at least partially vaporized prior to introduction into the unit.

8. A method for recovering and separating chemicals produced during sulfite pulping operations which comprises:
   passing liquors from said operations containing chemicals to be recovered and separated through a plurality of units containing activated-carbon;
   separating a first chemical from said liquors with a first activated-carbon containing unit;
   separating a second chemical from said liquors with a second activated-carbon containing unit; and
   separately recovering the first and second chemicals from their respective units containing activated-carbon by introducing a solvent into each unit and subsequently separating the chemical from the solvent.

9. A method, as claimed in claim 8, in which the chemical containing liquors are treated with steam prior to introduction into the units containing activated-carbon.

10. A method, as claimed in claim 8, in which two to four units containing activated-carbon are arranged in series.

11. A method, as claimed in claim 8, in which said chemical containing liquors are introduced into the activated-carbon containing unit as a vapor.

12. A method, as claimed in claim 8, wherein the solvent introduced into each unit for separately recovering the first and second chemicals is selected from the group consisting of methanol, ethanol, acetone and benzene.

13. A method, as claimed in claim 12 in which the solvent is at least partially vaporized prior to introduction into the unit.

* * * * *